United States Patent [19]
Haushalter et al.

[11] Patent Number: 5,602,266
[45] Date of Patent: Feb. 11, 1997

[54] MICROPOROUS SQUARE PYRAMIDAL-TETRAHEDRAL FRAMEWORK VANADIUM PHOSPHATES AND THEIR PREPARATION

[75] Inventors: Robert C. Haushalter, Little York, N.J.; Mohammad I. Khan, Skokie, Ill.; Linda M. Meyer, Easton, Pa.; Jon A. Zubieta, Syracuse, N.Y.

[73] Assignee: NEC Research Institute, Inc., Princeton, N.J.

[21] Appl. No.: 564,760

[22] Filed: Nov. 29, 1995

[51] Int. Cl.⁶ .................................................. C07F 9/02
[52] U.S. Cl. .................. 556/13; 556/17; 556/26; 556/42
[58] Field of Search .................. 556/13, 17, 26, 556/42

[56] References Cited

U.S. PATENT DOCUMENTS

| 4,956,483 | 9/1990 | Corcoran, Jr. et al. | 556/26 |
| 5,200,187 | 4/1993 | Haushalter et al. | 423/308 |
| 5,324,848 | 6/1994 | Haushalter et al. | 556/13 |

*Primary Examiner*—Porfirio Nazario-Gonzalez
*Attorney, Agent, or Firm*—Arthur J. Torsiglieri

[57] ABSTRACT

A new class of vanadium phosphate materials using a mixed valence pentavanadate as the building block has been created using hydrothermal self-assembly techniques. These materials use a framework composed solely of $V_5O_9(PO_4)_{4/2}$ pentamers and apart from the cationic template contain some of the largest voids and cavities yet reported in open framework solids.

4 Claims, 9 Drawing Sheets

MICROPOROUS SQUARE PYRAMIDAL-TETRAHEDRAL FRAMEWORK VANADIUM PHOSPHATES AND THEIR PREPARATION

This invention relates to novel vanadium phosphate materials useful to provide microporous structures and to the methods for the preparation of such materials. This invention was developed under work in connection with the United States National Science Foundation, Grant No. CHE 9318824. The United States Federal Government may have certain rights in the invention.

FIELD OF THE INVENTION

BACKGROUND OF THE INVENTION

There is currently intense interest in the chemistry of the vanadium oxide phosphate system because the system is capable of providing networks of connected vanadium and phosphorus polyhedra with a diversity of structures. This structural diversity is associated in part with the ability of vanadium oxygen coordination polyhedra to adopt tetrahedral, square pyramidal and octahedral geometries and to aggregate into larger cores by condensation of polyhedra through shared oxygen atoms. Further condensation with phosphate tetrahedra, such as $PO_4^{3-}$, $HPO_4^{2-}$ and $H_2PO_4^{-1}$ results often in complex polyhedral networks.

Moreover, when cationic templates are introduced, polyhedral framework solids with tunnels, cages and micropores may be isolated. Such solids offer considerable promise since they make possible microporous framework solids, capable of shape selective absorption like the zeolites and aluminophosphates, that are useful as catalysts or molecular sieves.

U.S. Pat. No. 5,324,848 which was issued on Jun. 28, 1994 describes several vanadium phosphate compounds that have been formed using hydrothermal self-assembly techniques that are characterized by a vanadium-phosphate framework and an alkali, alkaline-earth metal, or organoammonium cationic templates.

SUMMARY OF THE INVENTION

The present invention is the discovery of Complex networks, consisting solely of $V_5O_9(PO_4)_2$ pentamers, that absent the cations would contain some of the largest voids and apertures and the lowest framework metal atom densities yet reported in open framework solids.

The compositions of the invention are embraced within the generic formula

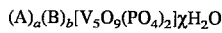

$(A)_a(B)_b[V_5O_9(PO_4)_2]\cdot\chi H_2O$ where A is one or more metals chosen from the group of alkali metals or alkaline-earth metals consisting of Li, Na, K, Rb, Cs, Mg, Ca, Sr and Ba and in which B is an organic template either of the form $R_4N^+$ or a cyclic ammonium cation of the general formula

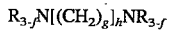

$R_{3-f}N[(CH_2)_g]_hNR_{3-f}$ where f is either 1 or 2, g is an integer at least one and preferably no greater than 4, and h is one greater than f in which R is one or more compositions chosen from the group consisting of H, $C_nH_{2n+1}$, $C_nH_{2n}NQ_3$ where n has a value equal to or less than 4 and Q is either H or $C_nH_{2n+1}$, and at least one of a or b has a value greater than zero to provide the cations that serve as the template about which forms the vanadium phosphate framework.

In particular, we have prepared square pyramidal-tetrahedral framework vanadium phosphates $[HN(CH_2CH_2)_3NH]K_{1.35}[V_5O_9(PO_4)_2]\cdot 2H_2O$, to be designated hereinafter as compound A, and $Cs_3[V_5O_9(PO_4)_2]\cdot 4.5H_2O$, to be designated hereinafter as compound B, as examples of this new class of such solids.

DETAILED DESCRIPTION OF THE INVENTION

Figure 1A:
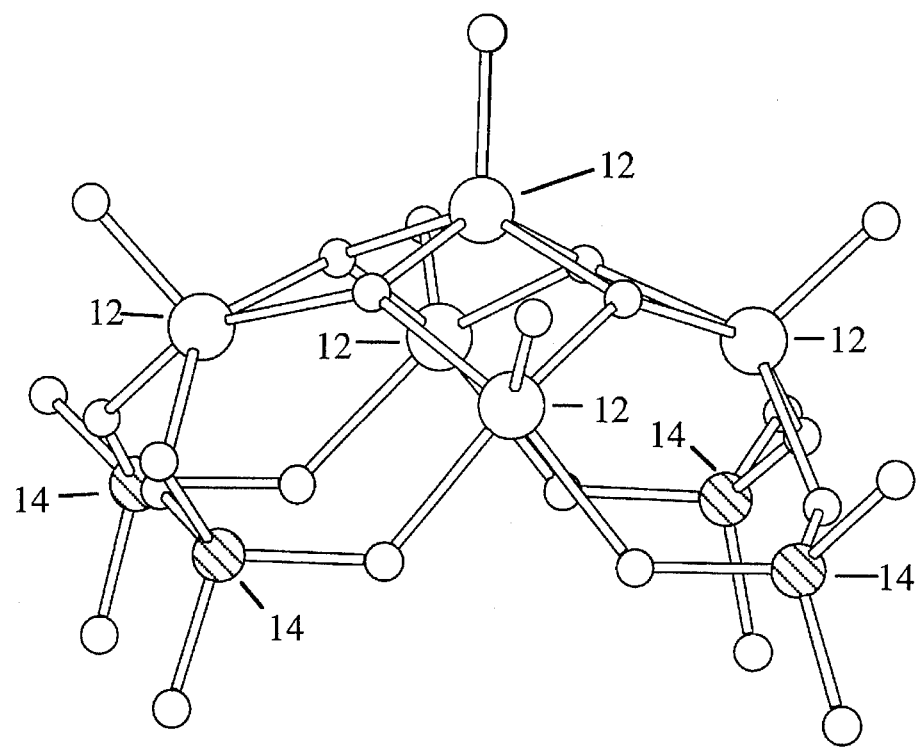
FIGS. 1A and 1B are respectively top and side views of the mixed valence pentameric $[V_5O_9(PO_4)_{4/2}]$ that serves as the basic building block of novel materials in accordance with the invention.
Figure 1B:
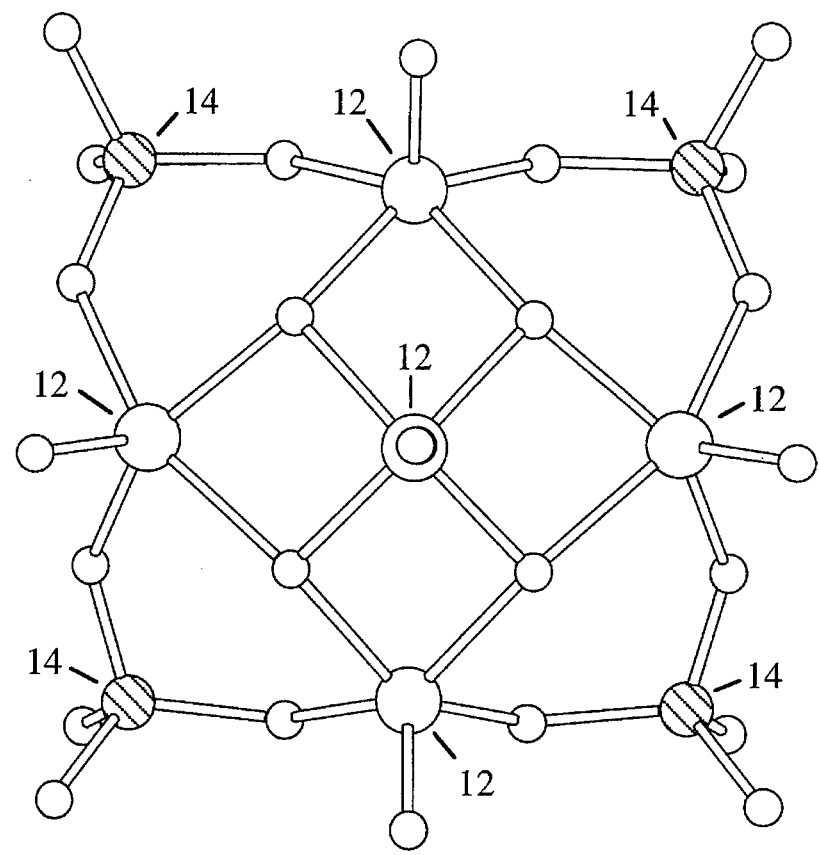

With reference now to the drawing, FIG. 1A and 1B are schematic representations of two views of the mixed valence pentavanadate cluster that serves as the building block of the novel materials of the invention. In particular, FIG. 1A is a view as viewed along a plane parallel to that formed by the four peripheral vanadium atoms and FIG. 1B a view along a plane perpendicular to that formed by these vanadium atoms. In each figure, the largest circles 12 represent vanadium atoms, the intermediate size hatched circles 14 represent the phosphorous atoms and the unnumbered smallest circles represent the oxygen atoms. The degree of curvature, size, shape and charge of the $[V_5O_9(PO_4)_2]$ building block, which resembles a portion of an arc of a circle, favors the formation of large cavities.

Compound A, $[HN(CH_2CH_2)_3NH]K_{1.35}[V_5O_9(PO_4)_2]\cdot \chi H_2O$, was prepared from the reaction of $KVO_3:N(CH_2CH_2)_3N:(CH_3CH_2)_2NH$:phenylphosphonic acid:$H_3PO_4:H_2O$ in a molar ratio of 1:2:2:0.75:2:100 for 4 days at 170° C. and was isolated in 75% yield as a single phase of perfectly formed, dark green-black rhombic dodecahedra. Utilizing a rotating anode X-ray source, the data were collected on a 40×40×40 μm³ crystal and the resulting structure solved by direct methods in space group $\bar{I}43m$. As best appears in FIG. 1B, the fundamental building blocks of the framework are $VO_5$ groups and these are present in the form of unusual cross-shaped $V_5$ pentamers that consist of a central $VO_5$ square pyramid sharing each of its four basal edges with edges from four additional square pyramidal vanadium centers. The pentamer is connected to four other $V_5$ units via 4/2 phosphate tetrahedra. Valence sum calculations give a value of 20.7+ for the five V atoms yielding a calculated framework charge of $[V_5O_9(PO_4)_2]^{-3.3}$ in good agreement with the −3.3 required if the diazabicyclooctane (DABCO) cations are fully protonated and the $K^+$ occupied as described. The $[V_5O_9(PO_4)_{4/2}]$ unit displays a large degree of curvature. The combination of this curvature, the tetrahedral coordination requirements of the P, the distance between the 4/2 $PO_4$ groups and the relatively low charge per volume in the pentamer, all favor metrically large structures that would have difficulty filling all space in a typically dense fashion.

Figure 2A:
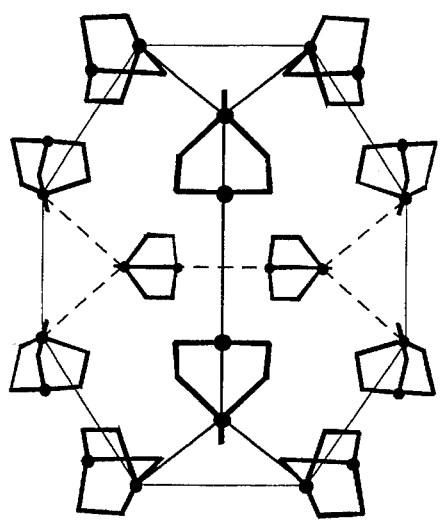
FIGS. 2A, 2B and 2C are schematic representations of the various contents of a large cavity formed within the pentameric framework of compound A described earlier.
Figure 2C:
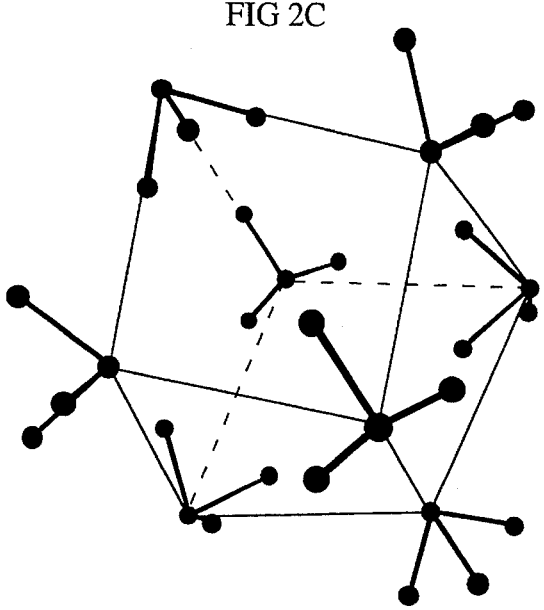
Figure 2B:
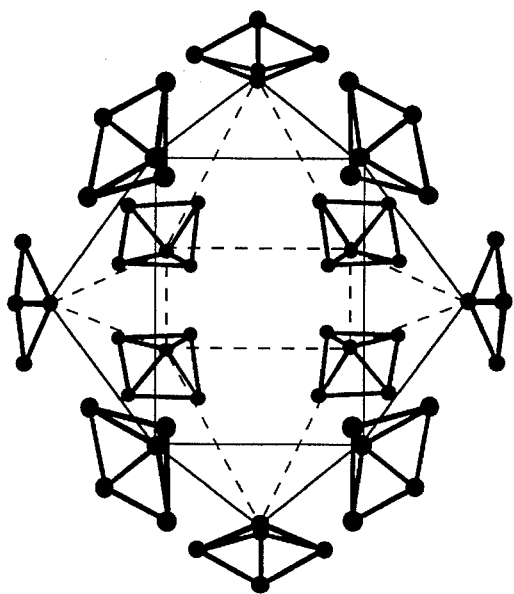
Figure 2D:
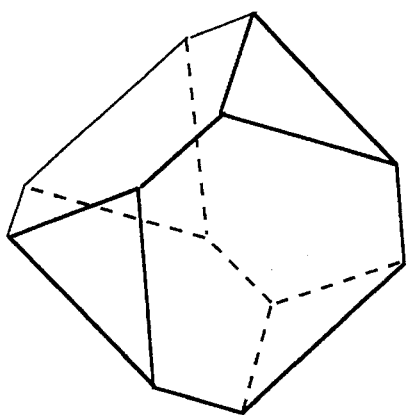
FIG. 2D represents the essence of the symmetry of the cavity.
Figure 3:
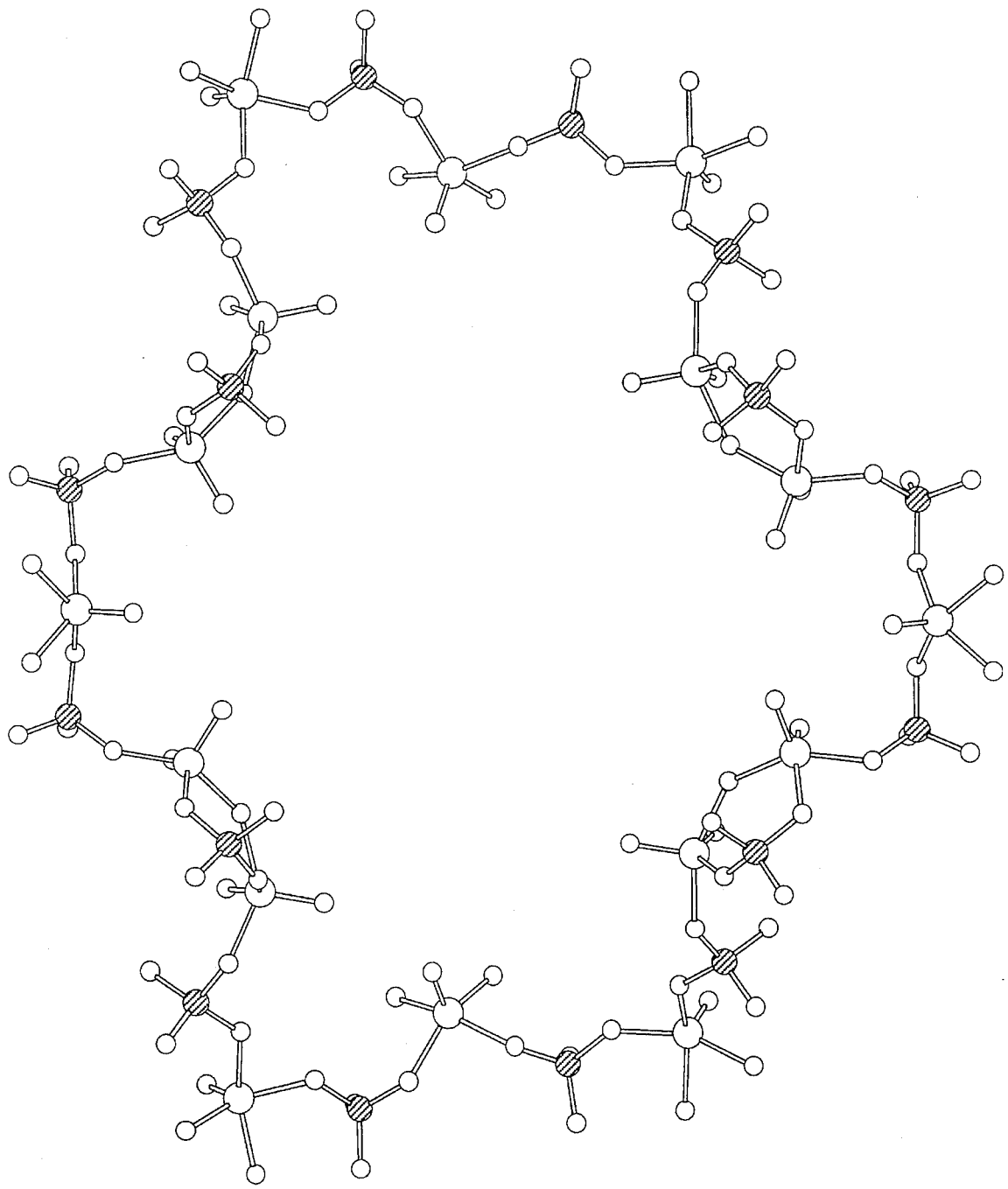
FIG. 3 is a cross-sectional view, taken perpendicular to one of the <110> directions of the 32-ring central sections of a large cavity formed within compound A.
Figure 4A:
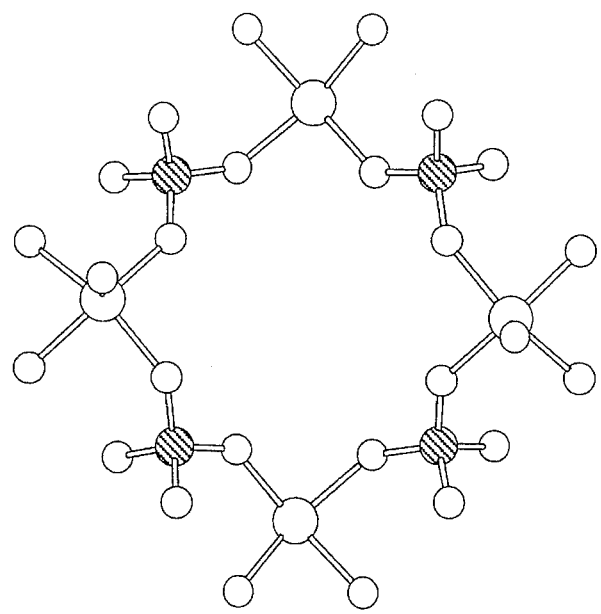
FIG. 4A is one of the 8-ring windows, which contains the $K^+$ cation ($K^+$ not shown), present in a small cavity in compound A.
Figure 4B:
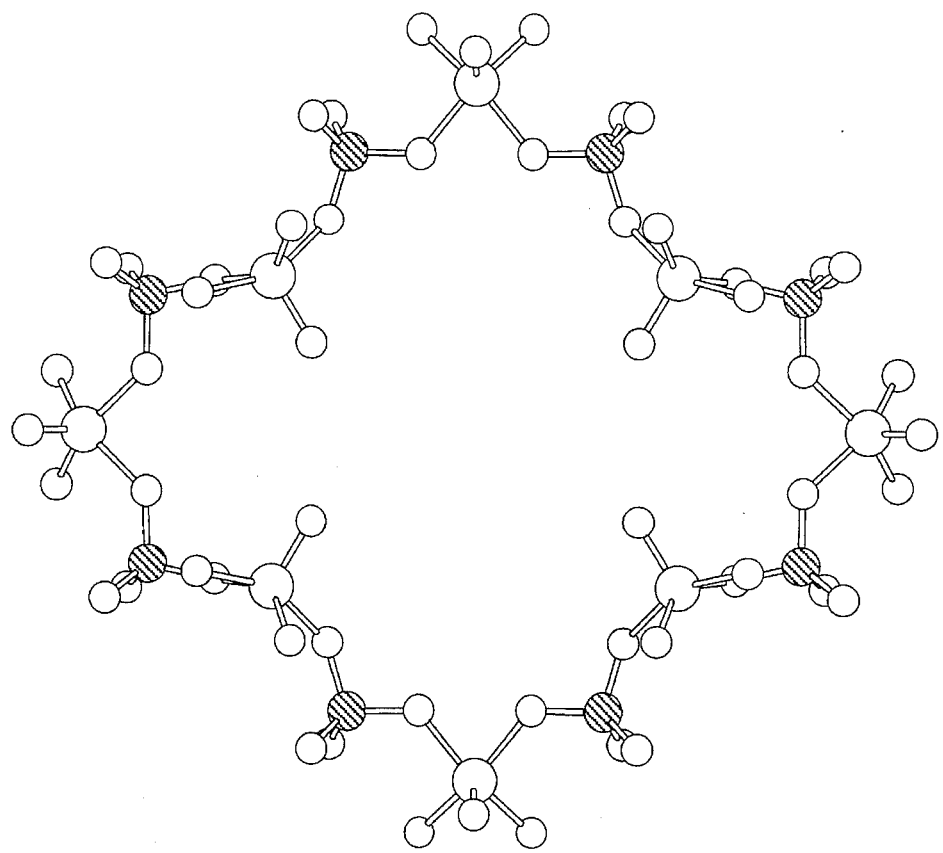
FIG. 4B is one of the rectangular 16-ring windows exiting a large cavity in compound A.

The most prominent feature of the $\bar{I}43m$ structure is the extremely large voids in the V—P—O framework, centered about 0, 0, 0 and 1/2, 1/2, 1/2, which have rigorous $\bar{4}3m$ site symmetry and are apparent in the projection of the unit cell contents down <100>. These cavities are filled in a remarkably complicated manner with a mixture of organic and inorganic cations and water. The center of the cavity contains an aggregate of twelve $HN(CH_2CH_2)_3NH^{2+}$ (1,4-diazabicyclooctane=DABCO) cations, as seen in FIG. 2A, that are arranged with the symmetry of a truncated tetrahedron, as shown in FIG. 2D. One N atom of each DABCO lies on each of the twelve vertices of a truncated tetrahedron. The twelve organic moieties are in turn surrounded by thirty-two $K^+$ cation sites that are present as eight tetramers as shown in FIG. 2C. All eight crystallographically equivalent tetramers are arranged in the form of two interpenetrating tetrahedra, one tetrahedron formed from four tetramers oriented toward the center of the cavity and one formed from four tetrareefs oriented outward from the center to give a tetrahedrally distorted cube with one tetramer on each corner of the cube. The organic cations, the inorganic $K^+$ cations and the water of crystallization are all enclosed within a cavity formed from twelve vanadium pentamers connected by phosphate groups and corners of many adjacent pentamers. The central V atoms of the twelve pentamers also lie at the vertices of a truncated tetrahedron, as shown in FIG. 2B. Thus for 1.35 $K^+$ and one DABCO per pentamer, there is a total of 40.2 positive charges per cavity, which agrees very well with the framework charge requirement of −39.6 from the vanadium valence sum calculations. The surprisingly large volume of these voids is reflected in the very low framework metal atom density. For compound A, there are only about 9.3M atoms (M=V, P) per 1000 $Å^3$ compared with values of about 12.7 and 11.1 atoms per 1000 $Å^3$ for the very open faujasite (M=Si) and cloverite (M=Ga, P), respectively, making compound A among the lowest framework density materials known. A cross sectional view of the cavity (FIG. 3) shows the enormous 32-ring present at the maximum diameter of the cavitye As in FIG. 17 the vanadium, phosphorus and oxygen atoms are represented, respectively, by the largest, intermediate and smallest circles. This is thought to be one of the largest contiguous apertures observed thus far in a solid state material. The interconnection of the large voids generates a fascinating tunnel topology. Each large cavity at 0, 0, 0 is connected to six other symmetry equivalent cavities along all <100> directions to give an array with simple cubic symmetry. As seen in FIG. 4B, each large cavity has six rectangular 16-ring windows, which have the planes of the rings perpendicular to the <100> directions, surrounding the origin in an octahedral fashion. The 16-ring windows, which are somewhat restricted in one direction from the terminal V=O groups that protrude into the window, have free dimensions (minimum O—O distance less one O radius of 2.6 Å) of about 9.4 by 4.4 Å. The large void at the origin is connected through the 16-ring window. s to its six neighboring large cavities via intervening smaller cavities which possess a free diameter of approximately 6.5 Å. As shown in FIG. 4A, these smaller voids, which contain 8-ring windows with a $K^+$ cation loosely centered in each window, lie on the midpoints of the unit cell edges half way between the large voids. Since the unit cell is body centered, there is a crystallographically equivalent set of voids, one at the origin and another centered about 1/2, 1/2, 1/2, but the array of tunnels and voids containing the cavity at the origin interpenetrates, but never intersects, the array containing the cavity at 1/2, 1/2, 1/2. A naturally occurring zeolite, paulingite, possesses an array of (much smaller) tunnels with a similar topology. To better comprehend these complicated tunnel geometries, we have employed a program that allows visualization of the isosurface that divides the framework from the void space within the open framework. The isosurface that lies between the framework atoms and the voids is determined by the two interpenetrating, but independent and nonintersecting tunnel networks, as well as the interconnection of each large cavity via intervening smaller cavities.

According to powder X-ray diffraction measurements, another phosphate $[H_2N(CH_2)_5]K_{1.35}$ $[V_5O_9(PO_4)_2]\cdot\chi H_2O$ (compound C), with a framework isocompositional to that found in compound A, but with charge-compensating piperidinium $H_2N(CH_2)_5^{1+}$ cations in place of DABCO, can be prepared as a single phase by substituting piperidine for DABCO in the synthesis. Charge balance is maintained by variation of the vanadium oxidation state in the framework.

More particularly, the process includes preparing a mixture of potassium vanadate, $KVO_3$, piperidine, $HN(CH_2)_5$, diethylamine, $(C_2H_5)_2NH$, phenylphosphonic acid, $C_6H_5P(O)(OH)_2$, $H_3PO_4:H_2O$ in the ratios of 1:3; 2:1:2:100 and heating to about 170° C. This treatment for eight days resulted in dark green crystals with a yield of 30%.

It seems clear that various other cations of the form $R_4N^+$ defined earlier can similarly be substituted in the synthesis for the inorganic portion of the template.

The vanadium phosphate supercage material $Cs_3$ $[V_5O_9(PO_4)_2]\cdot\chi H_2O$ (compound B), with $\chi$~4.5, was prepared from the reaction of $CsVO_3$:1,3-diaminopropane: $H_3PO_4:H_2O$ in a molar ratio of 3:5:5:2000 at 200° C. for 2 days and was isolated in 20% yield (based on V) as green-black cubes (about 5% of the isolated product is a brown solid that contains no V or P). In spite of the apparently essential requirement of the propanediamine in the reaction mixture, there was no indication from either the X-ray structure or elemental analysis (found 0.54% C and <0.1% N) that any organic cation was occluded. Instead, the voids were filled with inorganic $Cs^+$ and water molecules only. The framework of compound B was built up from the same pentamers as found in compound A, but connected together in an entirely different manner. Valence sum calculations indicate a total charge of 20.9+ for the five V atoms which gives a charge on the framework of −3.1 per formula unit agreeing well with the charge of 3+ provided by the three $Cs^+$ cations. Compound B crystallizes in the high symmetry cubic space group $Fd\bar{3}m$. As with compound A, there are large and small voids within the framework. Both types of cavity are surrounded by six $V_5$ pentamers that occupy positions corresponding to the face centers of a cube, with the V=O bond of the central V atoms in each pentamer lying on the lines that pass through the center of the cube and the midpoint of each face. The six pentamers are bridged together by portions of additional pentamers via intervening phosphate tetrahedra. The entire [V$_5$O$_9$(PO$_4$)$_{4/2}$] building block displays a pronounced bending with the V—V—V angles subtended at the apex of approximately 125° ±10° in compound B.

Figure 5:
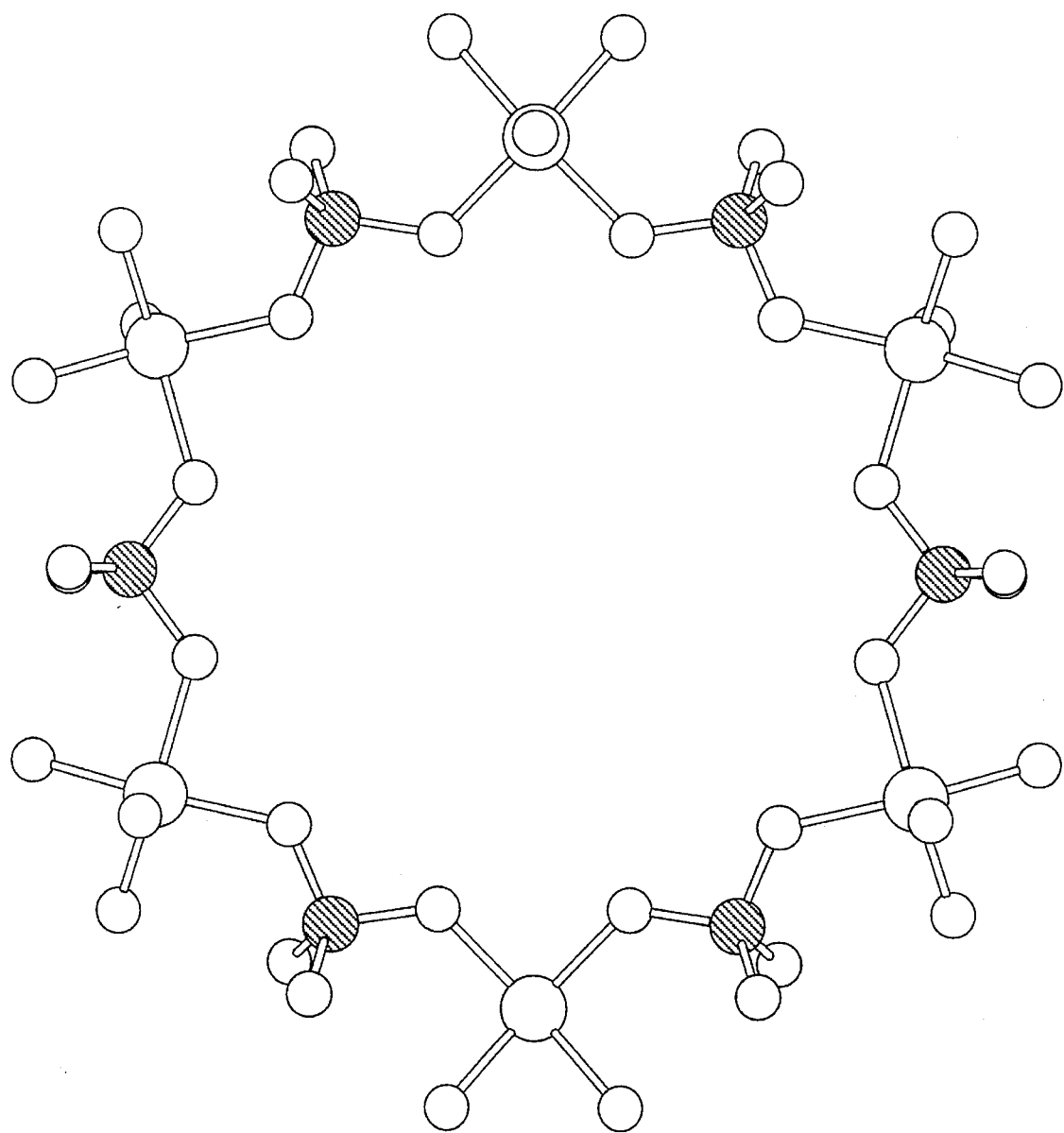
FIG. 5 is one of the four 12-ring apertures in each large cavity in compound B.
Figure 6A:
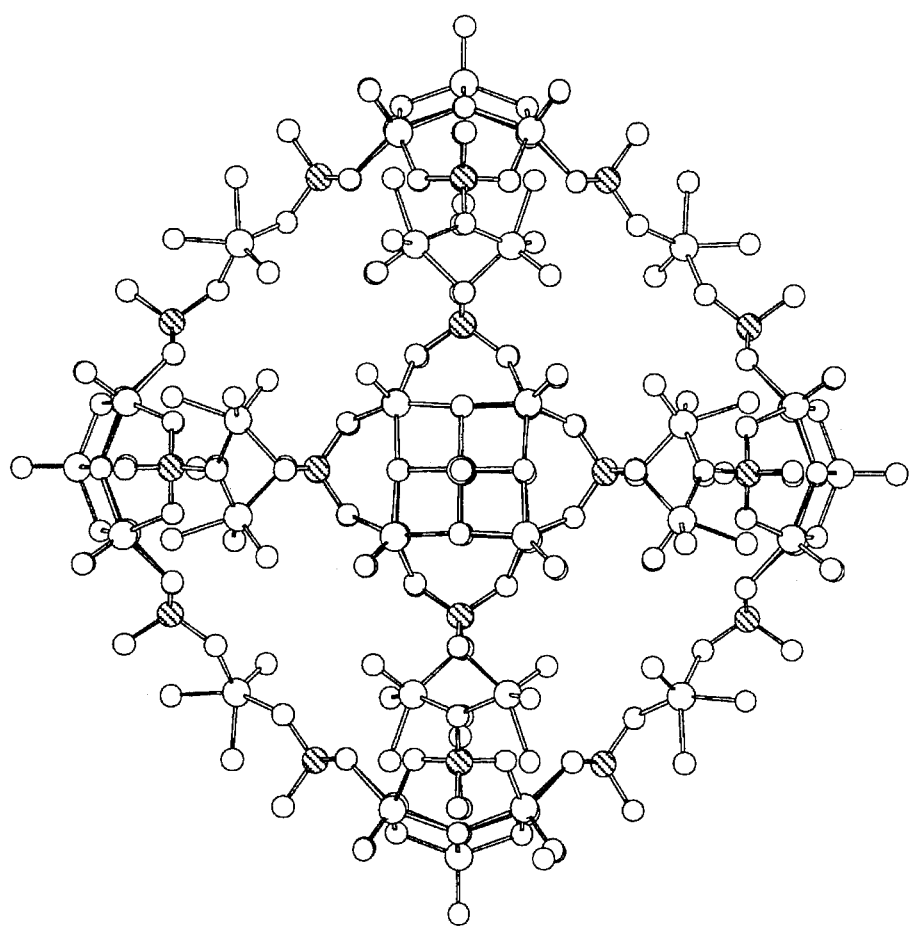
FIGS. 6A, 6B, 6C and 6D are different representations of the supercage in compound B.
Figure 6B:
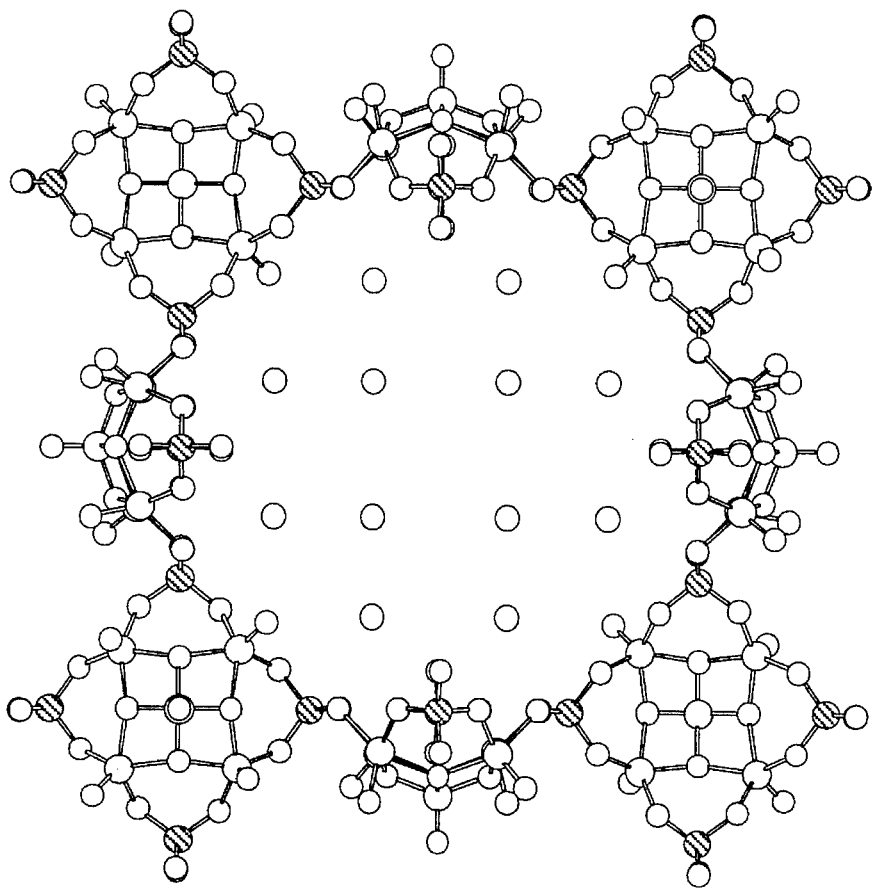
Figure 6C:
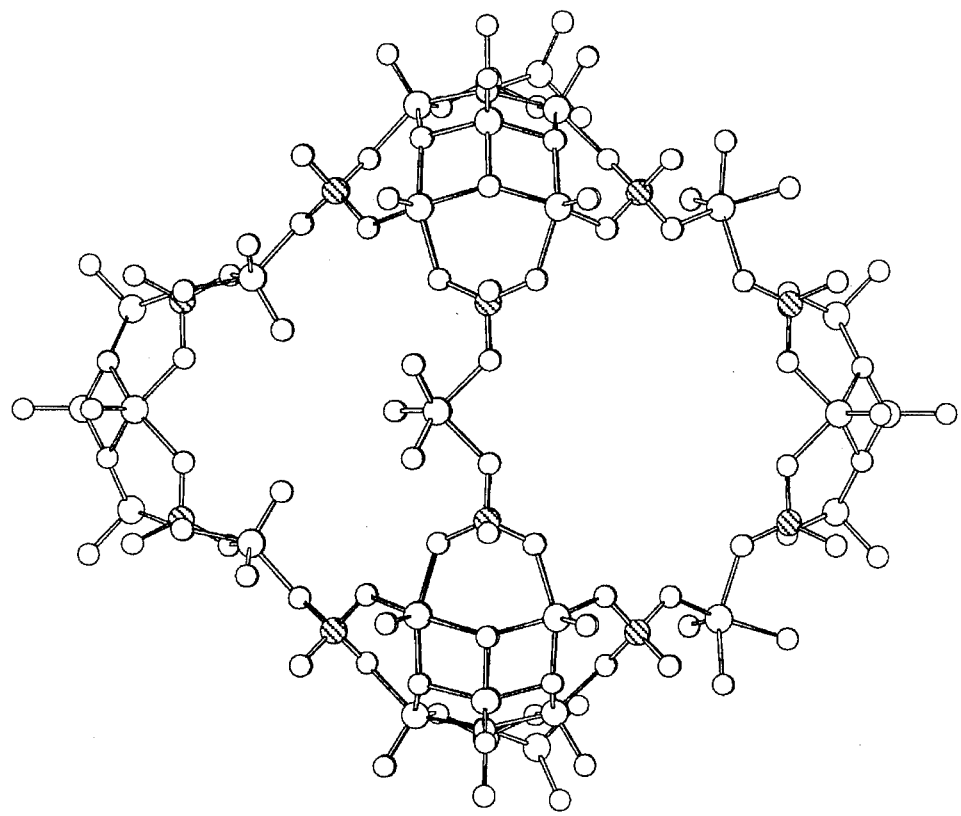
Figure 6D:
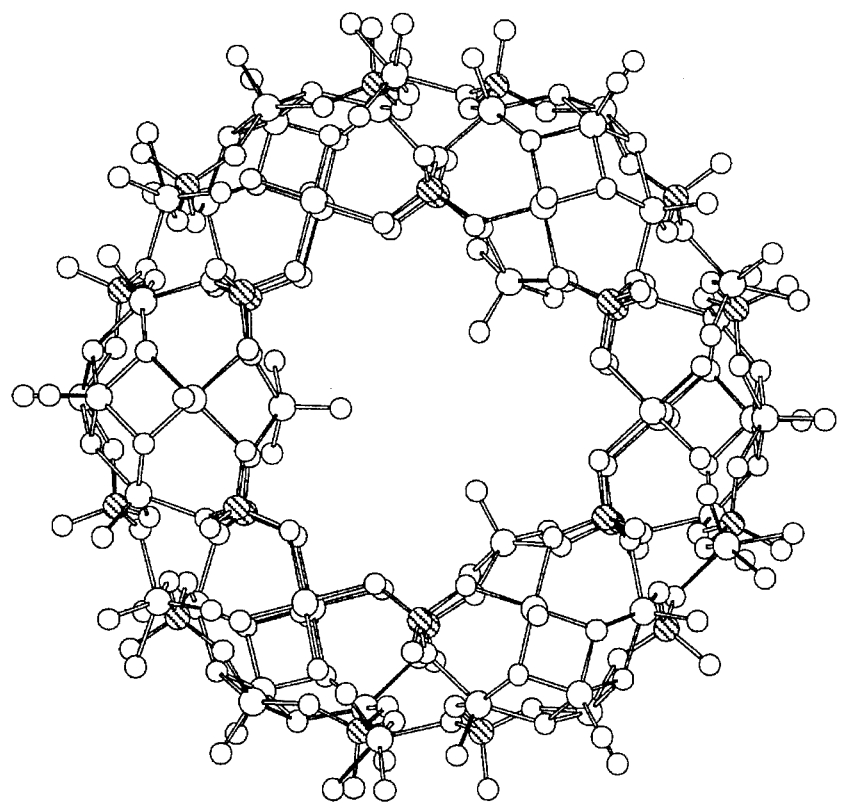
Figure 7:
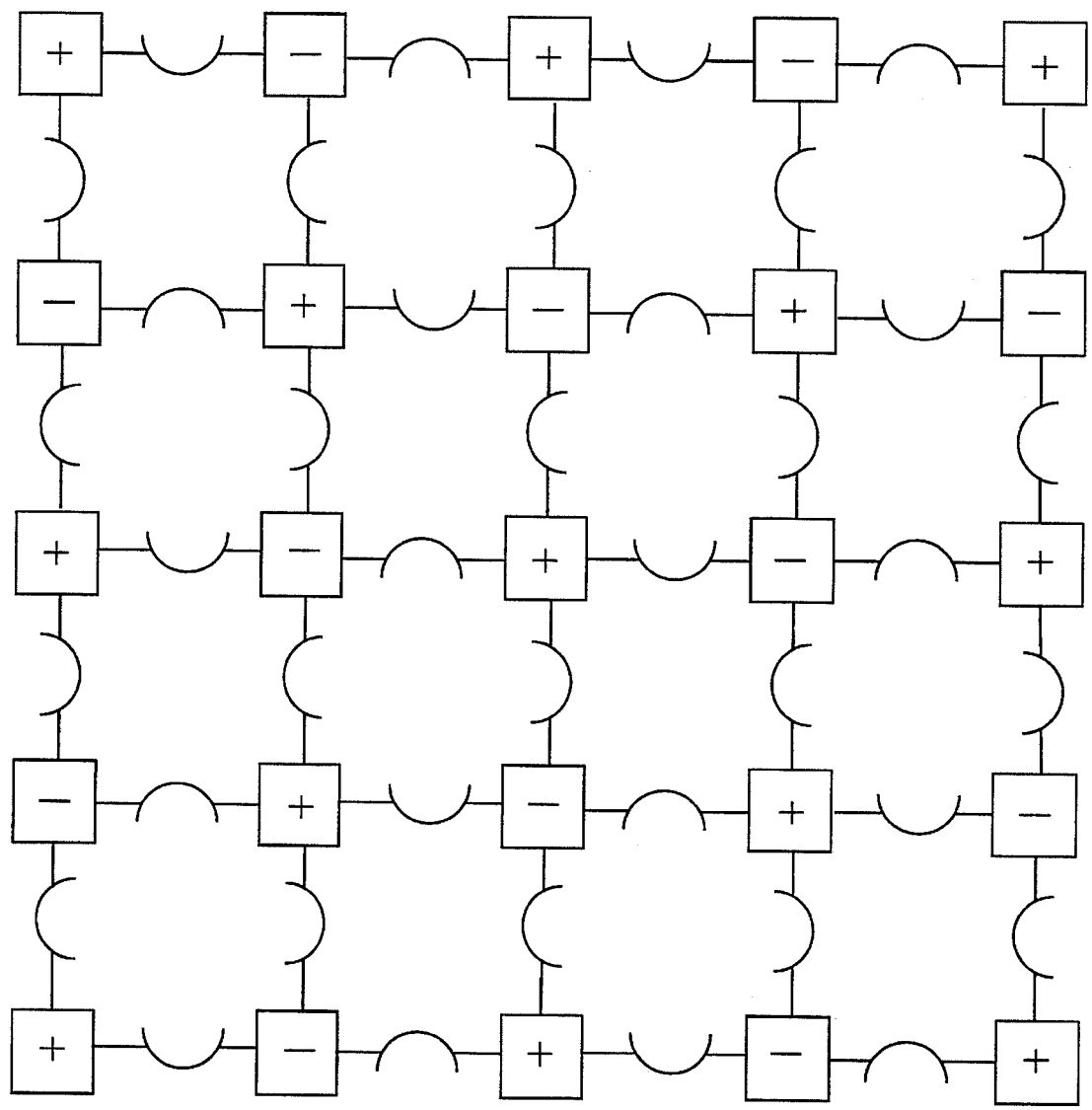
FIG. 7 is a schematic illustration for the building of compound B generated by stacking layers of $V_5O_9(PO_4)_2$ pentamers.

The large and small cavities differ in the orientation of the pentamer by having either all six pentamers curved outward or all six inward, i.e., the central V=O group oriented toward the exterior or interior of the cavity. The large and small cavities are arranged in a fashion analogous to the Na$^+$ and Cl$^-$ positions in the NaCl structure. When the six V$_5$ units are oriented outward, a very large cubic shaped cavity results with a minimum free diameter of approximately 14.3 Å and a body diagonal of 20 Å, as shown in FIG. 6A. The large cavities are connected to four neighboring cavities in a tetrahedral fashion with a topology identical to carbon atoms in diamond consistent with the fact that diamond and compound B both crystallize in space group Fd$\overline{3}$m. Each supercage is fused to four adjacent supercages via a twelve-ring window (maximum free diameter of 7.3 Å) the plane of which lies perpendicular to the <111> directions. The manner in which the Cs$^+$ cations are distributed within the void is shown in FIG. 6B. Thus there is a free path through a given supercage (and through the entire structure) defined by two of the 12-ring windows along a <110> direction, as shown in FIG. 5, as well as a second free path at 90° to this one. An isosurface representation of the large cavities and their connections to one another indicates an equal number of smaller cubic cavities, with the central V=O of each of the six pentamers oriented toward the interior of the cavity, that have free diameters between opposite V=O oxygen atoms of 5.3 Å. The manner in which the pentamers connect to form the 3-D lattice can be understood by examination of the schematic illustration of the lattice in FIG. 7.

This figure illustrates the construction of compound B where "+" represents a V$_5$ pentamer curved toward, and "−" represents one curved away from the plane of the page, while the arcs represent the direction of curvature for the pentamers viewed edge on. The structure is generated by stacking these "layers" in the proper registry and sequence such that the translational repeat corresponding to the unit cell would occur after every four layers. The layers would be stacked such that each "+" would be directly over a "−", but with a void from an intervening layer between, and all pentamers viewed edge on are related to the ones directly above and below it by a 4$_1$ screw axis as required by the space group symmetry.

Interestingly, another dark green materials with cubic unit cell parameters of 16.15 Å, exactly half that of compound B can be obtained under reaction conditions similar to those used to prepare it but substituting Na$^+$ for Cs$^+$. A single crystal X-ray structure determination of this new material, in space group Im$\overline{3}$m revealed a lattice of the same V$_5$ pentamer arranged in a manner similar to the pentamers in compound B, except that every pentamer site is two-fold disordered about the mirror plane containing the 4/2 P atoms of the phosphate groups. This disorder halves each axis of this new material relative to compound B in the representation of FIG. 7.

It seems clear that various other alkali metals or alkaline-earth metals can be used in place of the potassium, cesium and sodium to provide inorganic cations to fill the cavities in the vanadium phosphate framework.

Preliminary experiments indicate that the frameworks found in compounds A, B and C are relatively defect free and will readily undergo ion exchange reactions. For example, stirring compound C with a concentrated aqueous solution of either barium or ammonium chloride, conditions which will eventually cause dissolution of the compound, results in complete ion exchange within two hours according to electron microprobe and infrared absorption measurements. Moreover, water vapor absorption isotherms indicate that both compounds A and B are capable of sorbing large amounts of this gas. In particular, compound B displays a Type I absorption isotherm and takes up approximately 10 wt % water vapor. The value of $\chi$ in the formula Cs$_3$[V$_5$O$_9$(PO$_4$)$_2$]·$\chi$H$_2$O is 4.5 from the X-ray data which is in good agreement with the value obtained from the sorption measurements. The sorptive behavior of compound A is more complicated but much larger amounts of gas are absorbed.

What is claimed is:

1. A vanadium oxide phosphate composition characterized by a framework of V$_5$O$_9$(PO$_4$)$_2$ pentamers having the generic formula (A)$_a$(B)$_b$[V$_5$O$_9$(PO$_4$)$_2$]·$\chi$H$_2$O where A is one or more metals chosen from the group of alkali metals or alkaline-earth metals consisting of Li, Na, K, Rb, Cs, Mg, Ca, Sr and Ba, B is an organic template of the form R$_4$N$^+$ or a cyclic ammonium cation of the general formula R$_{3-f}$N[(CH$_2$)$_g$]$_h$NR$_{3-f}$ where f is either 1 or 2, g is an integer at least one and preferably no greater than 4, and h is one greater than f in which R is one or more materials chosen from the group consisting of H, C$_n$H$_{2n+1}$, C$_n$H$_{2n}$NQ$_3$ where n has a value equal to or less than 4 and Q is either H or C$_n$H$_{2n+1}$, and at least one of a and b is greater than zero and they are such as to provide charge neutrality to the compound.

2. A composition according to claim 1 having essentially the formula

[HN(CH$_2$CH$_2$)$_3$NH]K$_{1.35}$V$_5$O$_9$(PO$_4$)$_2$·$\chi$H$_2$O.

3. A composition according to claim 1 having essentially the formula

[H$_2$N(CH$_2$)$_5$]K$_{1.35}$V$_5$O$_9$(PO$_4$)$_2$·$\chi$H$_2$O.

4. A composition according to claim 1 having essentially the formula

Cs$_3$[V$_5$O$_9$(PO$_4$)$_2$]·$\chi$H$_2$O.

\* \* \* \* \*